(12) United States Patent
Goldstein et al.

(10) Patent No.: US 10,779,816 B2
(45) Date of Patent: Sep. 22, 2020

(54) ORTHOPEDIC IMPLANT, METHOD, AND KIT

(71) Applicant: Medline Industries, Inc., Mundelein, IL (US)

(72) Inventors: Scott Goldstein, Chicago, IL (US); Wes Reed, Libertyville, IL (US)

(73) Assignee: Medline Industries, Inc., Northfield, IL (US)

( * ) Notice: Subject to any disclaimer, the term of this patent is extended or adjusted under 35 U.S.C. 154(b) by 207 days.

(21) Appl. No.: 15/204,533

(22) Filed: Jul. 7, 2016

(65) Prior Publication Data

US 2018/0008263 A1    Jan. 11, 2018

(51) Int. Cl.
*A61B 17/064* (2006.01)
*A61B 17/80* (2006.01)
*A61B 17/00* (2006.01)

(52) U.S. Cl.
CPC ...... *A61B 17/0642* (2013.01); *A61B 17/8095* (2013.01); *A61B 2017/00867* (2013.01); *A61B 2017/0641* (2013.01)

(58) Field of Classification Search
CPC . A61B 17/064; A61B 17/0642; A61B 7/0643; A61B 17/0644; A61B 2017/0645; A61B 17/0682
USPC .......................................................... 606/75
See application file for complete search history.

(56) References Cited

U.S. PATENT DOCUMENTS

| | | | |
|---|---|---|---|
| 3,939,828 A * | 2/1976 | Mohr | A61B 17/68 606/221 |
| 4,848,328 A | 7/1989 | Laboureau | |
| 5,449,359 A | 9/1995 | Groiso | |
| 6,086,593 A | 7/2000 | Bonutti | |
| 6,652,592 B1 | 11/2003 | Grooms | |
| 6,773,437 B2 | 8/2004 | Ogilvie | |
| 6,823,871 B2 | 11/2004 | Schmieding | |
| 7,662,174 B2 | 2/2010 | Doubler | |
| 7,722,610 B2 | 5/2010 | Viola | |
| 7,824,426 B2 | 11/2010 | Racenet | |
| 8,133,230 B2 | 3/2012 | Stevens | |
| 8,496,662 B2 | 7/2013 | Novak | |
| D691,272 S | 10/2013 | Dacosta | |
| D695,402 S | 12/2013 | Dacosta | |

(Continued)

FOREIGN PATENT DOCUMENTS

WO    2013006778    1/2013

OTHER PUBLICATIONS

Trnka et al., "The Role of Calcanea Osteotomies for Correction of Adult Flatfoot," Clinical Orthopaedics and Related Research, No. 365, pp. 50-64 (Aug. 1999).

*Primary Examiner* — Matthew J Lawson
(74) *Attorney, Agent, or Firm* — Fitch, Even, Tabin & Flannery LLP

(57) ABSTRACT

Disclosed in an orthopedic implant that comprises a spacer portion having a superior portion and an inferior portion, and a staple portion. The staple portion is integral with the spacer portion and comprises a crown portion and first and second leg portions, the first and second leg portions having distal end that converge front the crown portion and that are composed of a material that has superelastic properties at body temperatures, whereby the first and second leg portions are configured to impart a compressive biasing force when the implant is installed with the legs under tension.

15 Claims, 8 Drawing Sheets

(56) References Cited

U.S. PATENT DOCUMENTS

| | | | |
|---|---|---|---|
| D705,930 S | 5/2014 | Cheney | |
| D720,456 S | 12/2014 | Dacosta | |
| D720,457 S | 12/2014 | Bono | |
| D740,424 S | 10/2015 | Dacosta | |
| 9,289,252 B2 | 3/2016 | Dacosta | |
| 9,855,036 B2 * | 1/2018 | Palmer | A61B 17/0642 |
| 10,064,619 B2 | 9/2018 | Palmer | |
| 10,105,134 B2 * | 10/2018 | Biedermann | A61B 17/0642 |
| 10,117,647 B2 * | 11/2018 | Cheney | A61B 17/0642 |
| 10,130,358 B2 | 11/2018 | Palmer | |
| 2006/0058802 A1 * | 3/2006 | Kofoed | A61B 17/0642 606/75 |
| 2007/0038303 A1 | 2/2007 | Myerson | |
| 2007/0239278 A1 * | 10/2007 | Heinz | A61F 2/4425 623/17.15 |
| 2008/0319443 A1 * | 12/2008 | Focht | A61B 17/0642 606/75 |
| 2009/0138096 A1 | 5/2009 | Myerson | |
| 2009/0177203 A1 | 7/2009 | Reiley | |
| 2011/0022099 A1 * | 1/2011 | Ashman | A61B 17/823 606/331 |
| 2012/0265301 A1 | 10/2012 | Demers | |
| 2013/0123935 A1 | 5/2013 | Hunt | |
| 2013/0231667 A1 | 9/2013 | Taylor | |
| 2014/0024002 A1 * | 1/2014 | Knight | A61B 17/0642 434/262 |
| 2014/0288663 A1 | 9/2014 | Borden | |
| 2014/0358187 A1 * | 12/2014 | Taber | A61B 17/0642 606/86 R |
| 2015/0133940 A1 * | 5/2015 | Palmer | A61B 17/0642 606/75 |
| 2015/0134063 A1 | 5/2015 | Steinmann | |
| 2015/0164564 A1 | 6/2015 | Reiley | |
| 2015/0216575 A1 | 8/2015 | Predick | |
| 2015/0335367 A1 | 11/2015 | Austin | |
| 2016/0066907 A1 * | 3/2016 | Cheney | A61B 17/0684 606/75 |
| 2016/0089138 A1 | 3/2016 | Early | |
| 2016/0106544 A1 | 4/2016 | McWilliam | |
| 2016/0113770 A1 | 4/2016 | Early | |
| 2016/0166301 A1 | 6/2016 | Papangelou | |
| 2018/0344316 A1 | 12/2018 | Palmer | |
| 2019/0046183 A1 * | 2/2019 | Hartdegen | A61B 17/0644 |

\* cited by examiner

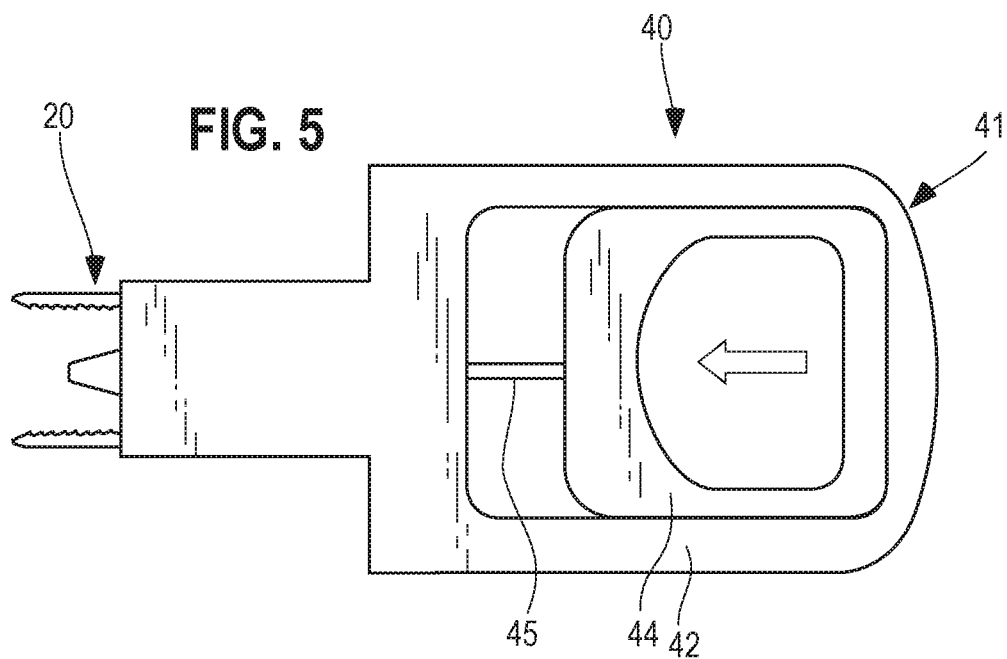
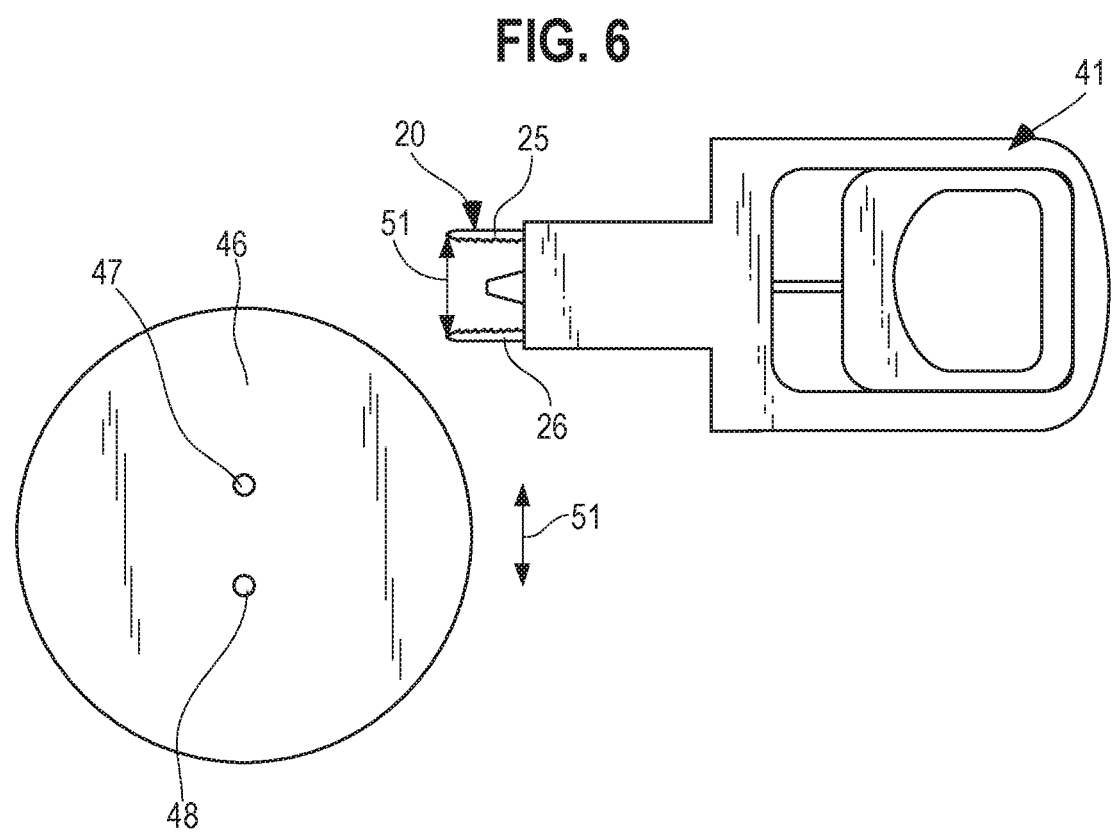

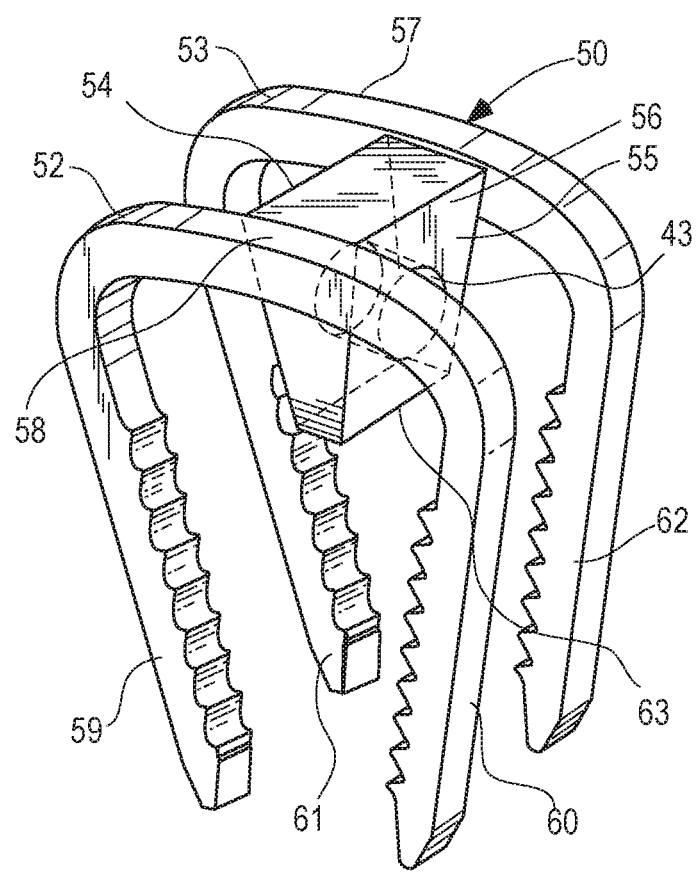

ORTHOPEDIC IMPLANT, METHOD, AND KIT

TECHNICAL FIELD

The invention is in the field of bone implants, and in certain embodiments relates to opening wedge implants used in osteotomy procedures.

BACKGROUND

Many osteotomy procedures have been devised, these including such procedures as the lateral column lengthening (Evans Osteotomy) and the plantarflexion osteotomy of the medial cuneiform (Cotton Osteotomy) for flatfoot correction. Such procedures generally involve cutting an opening in the bone of a patient, or between bone segments of a patient, and including a wedge or spacer to thereby lengthen the bone or maintain spacing between the bone segments. After the spacer has been inserted between the bone or bone segments, it is generally recommended to provide a means to retain the spacer in place while the bone heals in the case of allograft wedges, or indefinitely in the case of metal spacers. This is likewise necessary when creating an open wedge osteotomy at the base of the first metatarsal bone, a common procedure to address hallux vulgus (bunion deformity).

A number of implant-related devices are known for this purpose. A typical device comprises a plate with threaded openings for engaging bone screws that are screwed into the patient's bone. Some such plates are provided with integral metal wedges, although other such plates are provided without wedges for use with allograft bone wedges or for use with separate titanium bone wedges. While such structures may be successful in provided ancillary plate fixation, they can be difficult to install and ultimately can become uncomfortable for the patient. This is particularly true in foot surgeries, where plates used to secure them are very prominent on the bone and can cause soft tissue and nerve irritation, as the soft tissue structure on the lateral aspect of the calcaneous, the dorsal aspect of the medial cuneiform, and the medial aspect of the base of the first metatarsal are all limited. Given these side effects, in some instances, surgeons have placed wedges without the benefit of ancillary fixation, even though this approach is not recommended. It would be desirable to provide a spacer or spacer implant that is easier to install and more comfortable for the patient than the heretofore described approaches.

Generally, it has now been found that an implant that comprises a spacer portion and an integral staple portion, at least the staple portion comprised of a material that has superelastic properties when at the temperature of the human body, may now be provided. The spacer portion has a superior portion and an inferior portion. The staple portion has a crown portion and first and second leg portions that converge from the crown portion. The first and second leg portions are configured to provide a compressing biasing force when the implant is installed with the legs under tension.

BRIEF DESCRIPTION OF THE DRAWINGS

FIG. 5 is a side elevational view of a kit that includes the orthopedic implant shown in FIG. 1 positioned in an insertion tool.

FIG. 6 depicts a kit that comprises the kit of FIG. 5 and additionally template.

FIG. 7 is a perspective view of an orthopedic implant in accordance with a second embodiment.

Terms of orientation are for convenient reference to the drawings and are not intended to limit the orientation of the implant in use.

DESCRIPTION

In general, an orthopedic implant having a spacer portion, or wedge, and a staple portion is provided. The spacer portion has a superior portion and an inferior portion. The staple portion has a first crown portion and first and second leg portions, the first and second leg portions having distal ends that converge from the first crown portion. The first crown portion is connected into the spacer portion proximal to the superior portion. The spacer portion extends in the inferior direction generally towards the distal end of the first and second legs. At least the staple portion, and preferably the entire implant, comprise a material that has superelastic properties, such as many known nickel-titanium alloys ("Nitinol"). The implant is installed into a patient while the legs are under tension, whereby, given the superelastic composition of the leg portions, the first and second leg portions are configured to impart a compressive biasing force on the bone structure of the patient. Via this approach, the implant is resistant to becoming dislodged and the implant creates ancillary support for the spacer portion.

Figure 1:
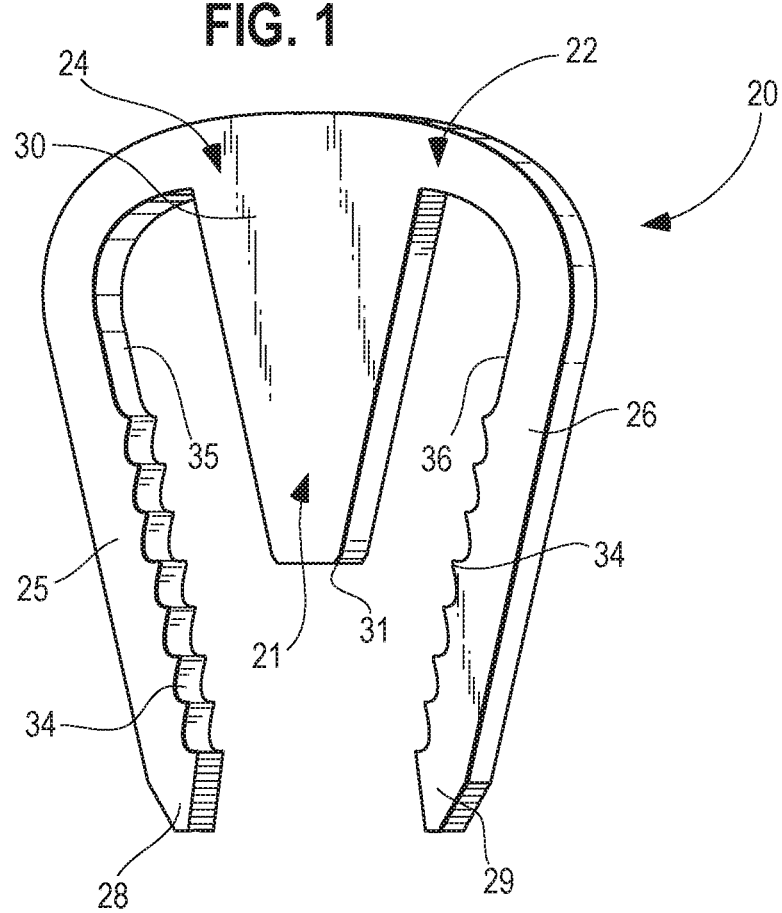
FIG. 1 is a perspective view of an orthopedic implant in accordance with one embodiment.
Figure 2:
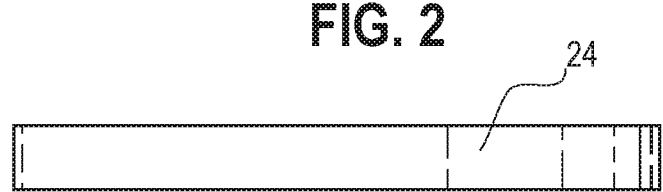
FIG. 2 is a top plan view of the orthopedic implant shown in FIG. 1.

As depicted in FIG. 1, the exemplary implant 20 comprises a spacer portion 21 and a staple portion 22, these portions being integral with one another, and, in the illustrated embodiment; composed monolithically of a superelastic nickel-titanium alloy. The staple portion comprises a crown portion 24 and first and second leg portions 25, 26. The first and second leg portions 25, 26 have respective distal ends 28, 29 that converge from the first crown portion 24, The crown portion 24 is connected to the spacer portion 21 proximal to the superior portion 30 of the spacer portion. As illustrated, the spacer portion 31 extends from the superior portion 30 to the inferior portion 31 in the inferior direction generally towards the distal ends 28, 29 of the first and second leg portions 25, 26. The crown portion 24 of the staple portion 22 is disposed in a position superior to the superior portion 30 of the spacer portion 21.

Figure 3:
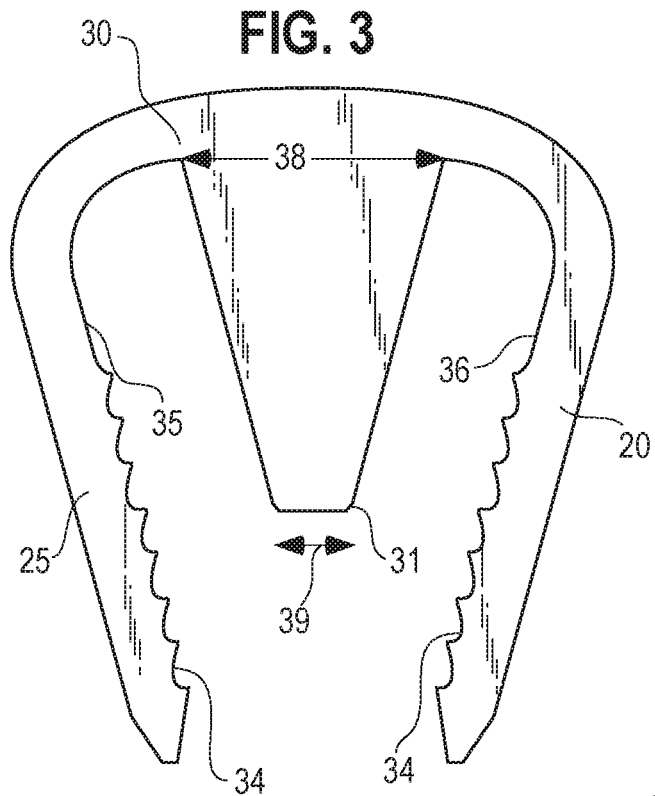
FIG. 3 is a side elevational view of the orthopedic implant shown in FIG. 1.

As also illustrated in FIG. 1 and as further shown in FIG. 3, each of the first and second leg portions 25, 26 has a bone retaining feature, which, in the illustrated embodiment, comprises a plurality of barbs 34 disposed on the inner surfaces 35, 36 of the leg portions 25, 26. With further reference to FIG. 3, the superior portion 30 has a greater lateral dimension 38 than the lateral dimension 39 of the inferior portion 31 to thereby impart a wedge shape to the spacer portion. In practice, the lateral dimensions of the superior and inferior portions 30 and 31, the lateral extent of the crown portion 24, and the lengths of the legs 25, 26 may be varied substantially and an implant manufacturer may provide several sizes to accommodate various patients and types of operations.

Figure 4:
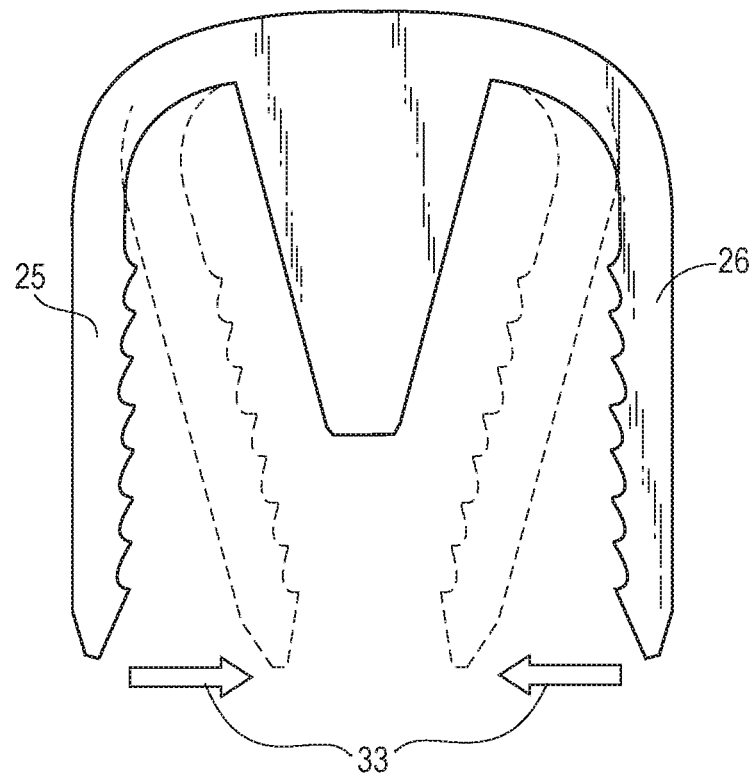
FIG. 4 is a side elevational view of the orthopedic implant shown in FIG. 1, showing the legs of the staple portion of the implant in tension.

The material is composed of a superelastic material, generally a metal alloy, such as Nitinol, a nickel-titanium alloy. Superelasticity is a well-recognized phenomenon of certain alloys in which the material deforms reversibly in response to an applied stress. For the present implants, the material should be superelastic at the normal body temperature of the intended patient, which, in the case of human patient, is in the range of about 95 degrees to 100° F. Generally, the superelastic property of the material when at this temperature causes the legs 25, 26 to bias inwardly as illustrated by arrows 33 in FIG. 4 when moved to a more open position. Via this approach, the first and second portions are configured to impart a compressive biasing force when the implant is installed with the legs under tension.

In use, the implant typically is provided in the form of a kit, which, as shown in FIG. 5, may be kit 40, The kit 40 shown in FIG. 5 comprises the implant 20 and an insertion tool 41 that releasably holds the implant and that maintains the first and second legs in tension via clips or other suitable retainers (not shown). The illustrated insertion tool 41 is intended to be exemplary and is typical of tools known for insertion of conventional surgical staples, and, as supplied, it retains the implant 20 with the legs in tension relative to the original state of the legs. The tool 41 comprises a handle 42 and plunger 44 with biasing rod 45, and is configured such that, when the plunger 44 is manually depressed, the biasing rod 45 moves relative to the handle 42 and urges the implant 20 to separate from the insertion tool blank. Preferably, as shown in FIG. 6, the kit 40 further includes a drilling template 46 having first and second pilots 47, 48 that are generally spaced apart at the same distance 51 that separates the first and second leg portions 25, 26 for positioning of pilot holes. Other configurations for the insertion tool, template, and kit are possible. For instance, it is contemplated that a kit may include multiple implants of varying sizes. As illustrated, the drilling template is substantially planar, although in some embodiments (not shown) the drilling template may be provided with its own spacer to assist in placement of the template. If multiple implants are available having spacers of differing sizes, then drilling templates having differently sized spacers may be used to gauge the best spacer size to be selected.

The form of the implant is not limited to a staple with two legs, and thus, for example, the implant may take the form of implant 50 shown in FIG. 7. In this embodiment the implant comprises first and second staple portions 52, 53 each integral with a spacer portion 55 and each comprising a material that has superelastic properties at body temperatures. Like that of the implant 20, each of the staple portions 52, 53 comprises a crown portion and leg portions 59, 60 and 61, 62 that each converge from the respective crown portions and that are configured to impart a compressive biasing force when the implant is installed with the legs under tension. In this implant, the spacer portion 55 bridges the crown portions 57, 5$ of the first and second staple portions 52, 53 and the wedge profile is disposed parallel to the central planes of the staples, although in some embodiments the wedge profile can be disposed laterally or at an angle relative to the staples. In this embodiment the superior transverse edges 54, 56 of the spacer portion 55 are generally parallel and have the same dimension as one another, and the inferior transverse edges (one shown at 63) are generally parallel to one another and have the same dimension as one another, the dimension of the superior edges being greater than that of the inferior edges.

As illustrated in FIG. 7, spacer portion 55 may include an optional graft window 45 (shown in hidden lines). Graft window 45 may be packed with bone graft prior to installation to assist with the formation of a solid bone bridge through the spacer portion to fuse the bone portions adjacent the spacer portion 55.

Generally, the illustrated implants are useful for in osteotomy and other surgical procedures not limited to the heretofore enumerated procedures. The surgical method generally comprises surgically exposing one or more bones or bone segments in the patient, cutting the bone to create an opening suitable for insertion of the spacer, and installing an implant as described hereinabove. Using the insertion tool, the spacer is positioned in the opening between the bones or bone segments, and the legs of the staple are positioned in the bone of the patient in a matter sufficient to impart a compressive biasing force on the bones or bone segments to thereby provide ancillary fixation for the spacer portion. The implant is then released from the insertion tool and the patient is allowed to recover from the procedure. The staple portion or portions are inhibited from release from the bone or bone segments via the bone retaining feature.

Figure 8:
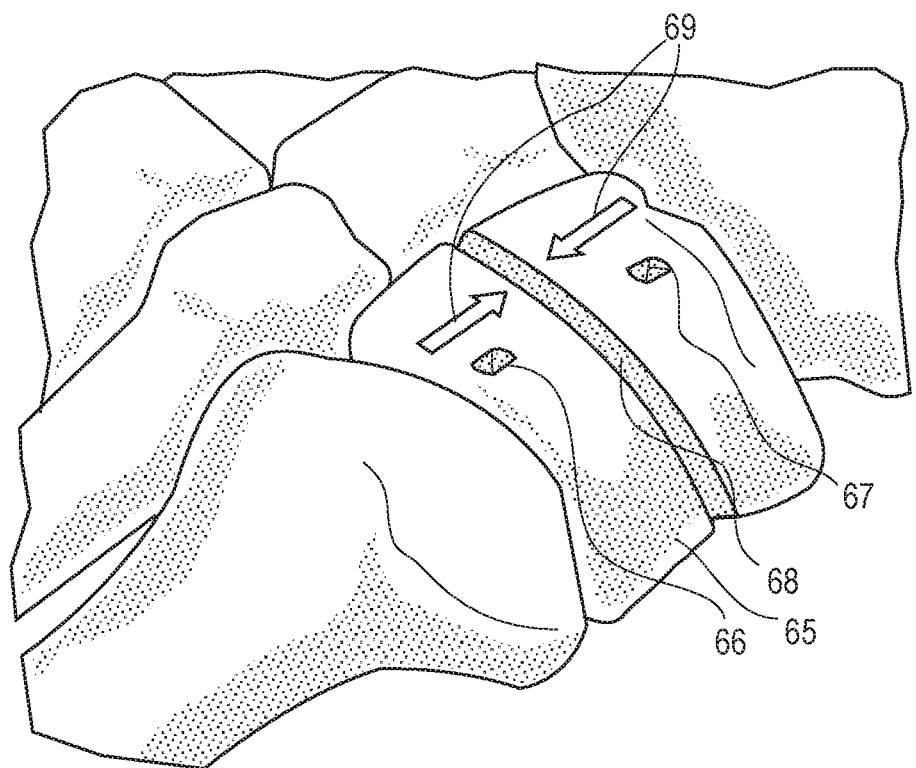
FIG. 8 is a plan view of the surgical region of a patient's medial cuneiform with a portion of the patient's bone removed in preparation for insertion of an orthopedic implant as part of an osteotomy procedure, and with pilot holes drilled for the staple legs.
Figure 9:
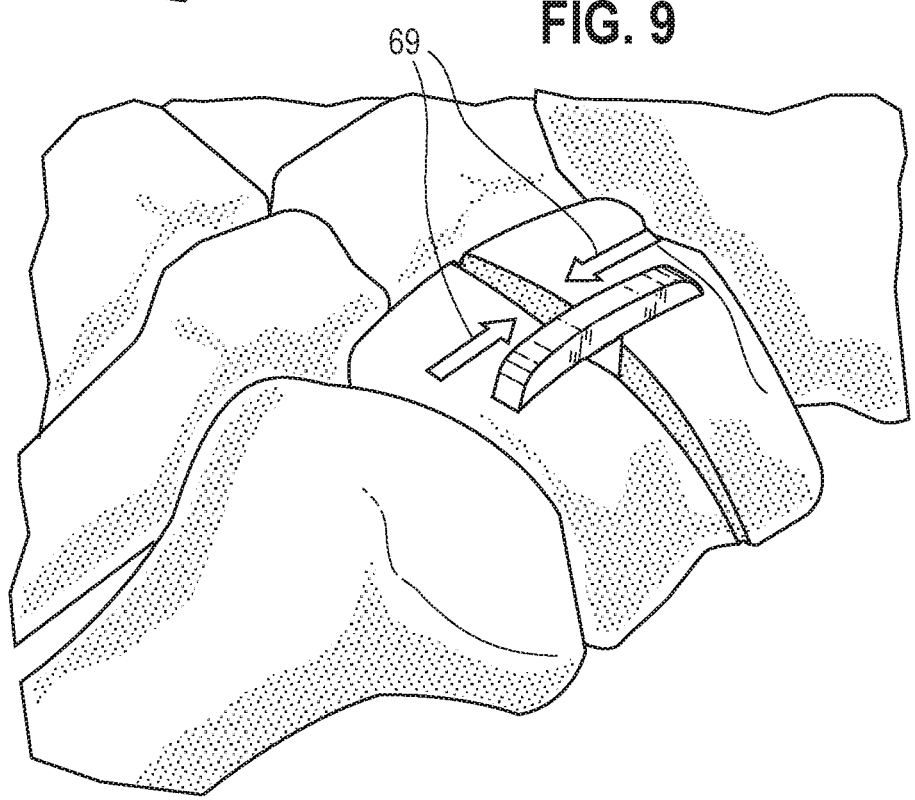
FIG. 9 is a plan view of a patient's surgical region after the implant has been installed as part of the osteotomy procedure.
Figure 10:
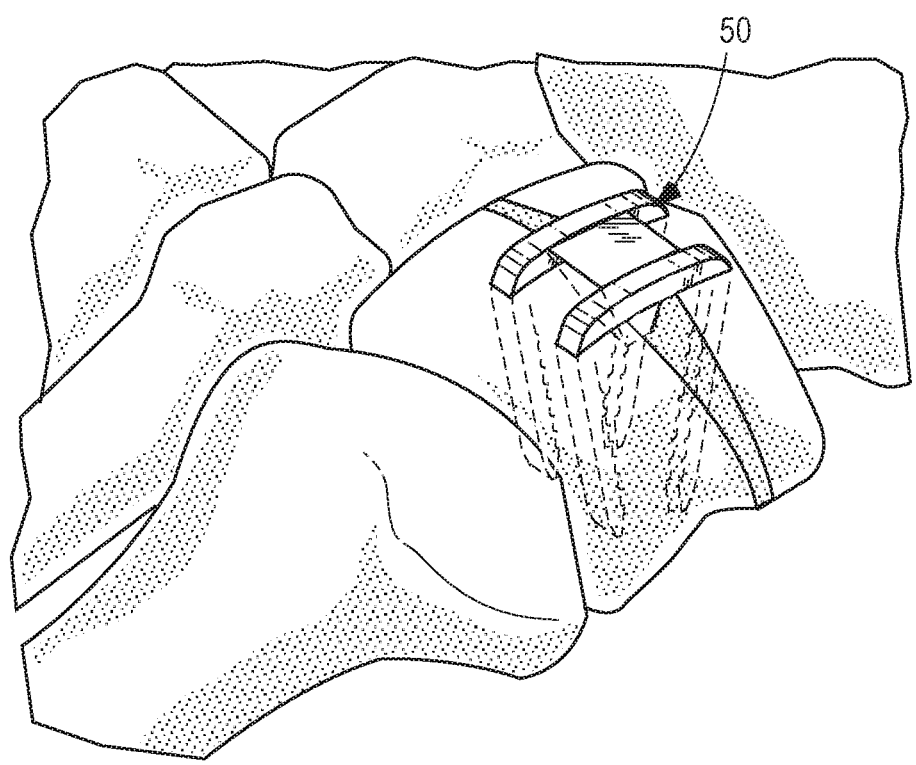
FIG. 10 is similar to FIG. 9 but depicting the surgical region after installation of the implant of FIG. 7 in a Cotton Osteotomy procedure.
Figure 13:
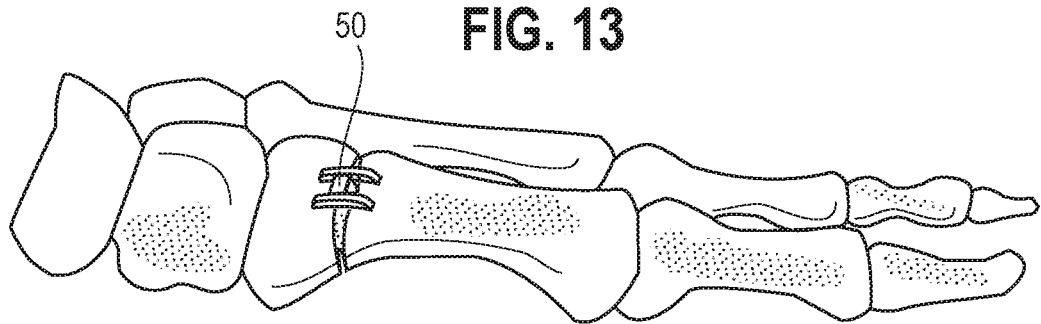
FIG. 13 depicts a surgical region after the installation of a base opening implant for correction of Hallux Valgus.

With reference to FIG. 8, for instance, the patient's bone 65 has been prepared for an osteotomy procedure, wherein an opening 68 is sized to receive a wedge-shaped spacer portion of the implant 20 shown in FIG. L Using the drilling template, pilot holes 66, 67 have been drilled into the bone, as shown in FIG. 8. The implant is then installed, leaving the configuration shown in FIG. 9. The legs of the staple portion exert a compressive force, represented by arrows 69, on the patient's bone or bone segments for provision of ancillary fixation. The same may be accomplished with the implant of FIG. 7, as depicted in FIG. 10 in a Cotton Osteotomy procedure or in FIG. 13 in a base opening procedure for correction of a hallux valgus deformity. In either case, a paste or putty made of bone or other suitable material may be used to fill in any gaps proximal the spacer after installation thereof.

Figure 11:
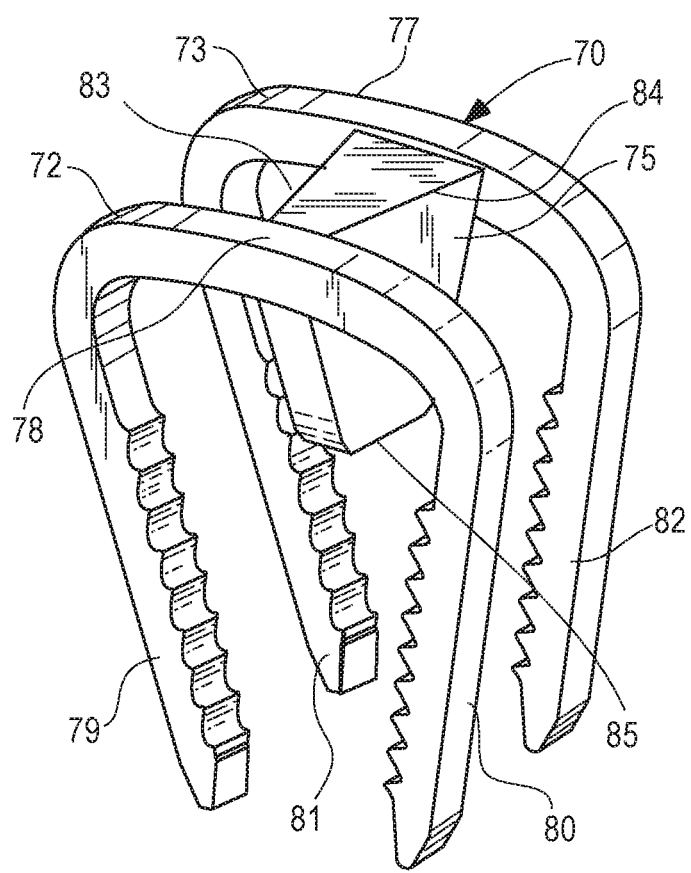
FIG. 11 illustrates an alternative embodiment of an orthopedic implant.
Figure 12:
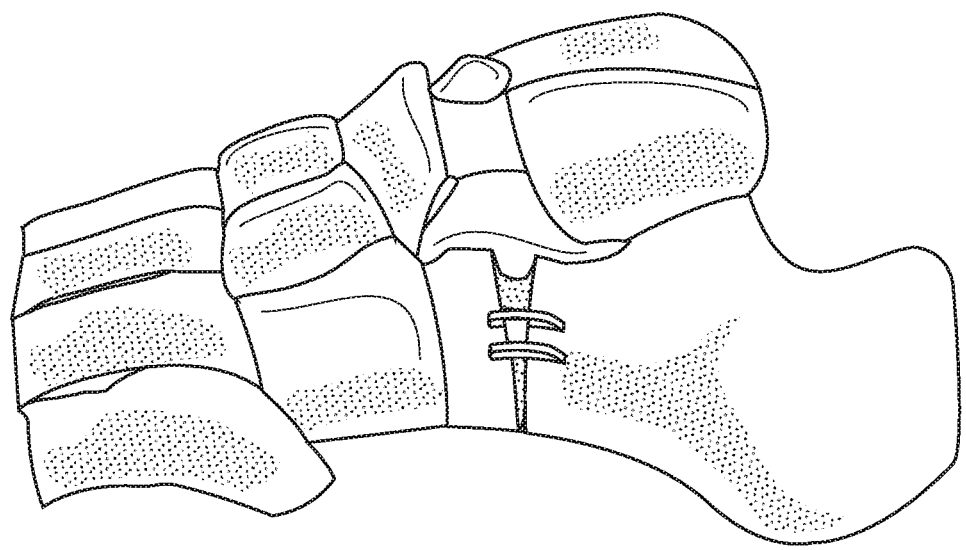
FIG. 12 depicts a surgical region after the installation of the implant of FIG. 11 in an Evans Osteotomy procedure.

With reference to FIG. 11, the illustrated alternative implant 70 comprises first and second staple portions 72, 73 each integral with a spacer portion 75 and each comprising a material that has superelastic properties at body temperatures. Like that of the implant 20, each of the staple portions 72, 73 comprises a crown portion 77, 78 and leg portions 79, 80 and 81, 82 that each converge from the respective crown portions 77, 78 and that are configured to impart a compressive biasing force when the implant is installed with the legs under tension. In this implant, the spacer portion 75 bridges the crown portions 77, 78 of the first and second staple portions 72, 73 and the wedge profile is disposed transversely to the central planes of the staples. In this embodiment, the spacer portion 75 has a tapered wedged profile such that it is wider at a portion adjacent staple 73 than at a portion adjacent staple 72. The implant of this embodiment may be useful in the performance of an Evans Osteotomy, as shown in FIG. 12, because the narrower wedge dimension at the inferior, or plantar, aspect of the osteotomy minimizes stress placed on the adjacent calcaneocuboid joint. In this embodiment, the superior transverse edges 83, 84 are converging and the inferior transverse edges (one shown at 85) are likewise converging. As shown, the inferior and superior edges all have the same dimension.

The illustrated implants are believed to provide ancillary stability for the spacer portion, and to be more comfortable to the patient than conventional bone plates.

Uses of singular terms such as "a," "an," are intended to cover both the singular and the plural, unless otherwise indicated herein or clearly contradicted by context. The terms "comprising," "having," "including," and "containing" are to be construed as open-ended terms. Any description of certain embodiments as "preferred" embodiments, and other recitation of embodiments, features, or ranges as being preferred, or suggestion that such are preferred, is not deemed to be limiting. The invention is deemed to encompass embodiments that are presently deemed to be less preferred and that may be described herein as such. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. No unclaimed language should be deemed to limit the invention in scope. Any statements or suggestions herein that certain features constitute a component of the claimed invention are not intended to be limiting unless reflected in the appended claims. Neither the marking of the patent number on arty product nor the identification of the patent number in connection with any service should be deemed a representation that all embodiments described herein are incorporated into such product or service.

What is claimed is:

1. An orthopedic implant comprising:
   a spacer portion having a superior portion and an inferior portion; and
   a first staple portion, said staple portion being integral with the spacer portion, said first staple portion comprising a first crown portion and first and second leg portions, the first and second leg portions having distal ends that converge from the first crown portion, said first crown portion being connected to the spacer portion proximal said superior portion, the spacer portion extending beyond the first crown portion in the inferior direction generally towards the distal ends of the first and second leg portions;
   at least said first staple portion of said implant comprising a metal material that has superelastic properties at body temperatures, wherein the distal end of the first leg portion is sized to be receivable within a bone hole in a first bone segment and the distal end of the second leg portion is sized to be receivable within a bone hole in a second bone segment, wherein said first and second leg portions are configured with inner surfaces that impart a compressive biasing force when the implant is installed with the legs under tension, and wherein the spacer portion is configured to maintain a spaced apart relationship between the first and second bone segments,
   further comprising a second staple portion integral with the spacer portion and comprising a material that has superelastic properties at body temperatures, said second staple portion comprising a second crown portion and third and fourth leg portions, the third and fourth leg portions having distal ends that converge from the second crown portion, said second crown portion being connected to the spacer portion proximal said superior portion and being spaced apart from said first crown portion of said first staple portion, whereby said third and fourth leg portions are configured to impart a compressive biasing force when the implant is installed with the legs under tension.

2. The orthopedic implant of claim 1, wherein the inner surface of each leg portion has a bone-retaining feature.

3. The orthopedic implant of claim 2, the bone-retaining-feature comprising a plurality of barbs.

4. The orthopedic implant of claim 1, the superelastic material comprising a nickel-titanium alloy.

5. The orthopedic implant of claim 1, said superior portion having a greater lateral dimension than said inferior portion to thereby impart a wedge shape to said spacer portion.

6. The orthopedic implant of claim 5, the spacer portion having superior transverse edges that are generally parallel to one another.

7. The orthopedic implant of claim 5, the spacer portion having a graft window traversing the spacer portion in a direction generally perpendicular to the transverse edges.

8. The orthopedic implant of claim 5, the spacer portion having superior transverse edges that are converging.

9. The orthopedic implant of claim 1, the crown portion of said first staple portion being superior to the superior portion of said spacer portion.

10. The orthopedic implant of claim 1, the spacer portion having a tapered wedged profile.

11. The orthopedic implant of claim 1, said superior portion having a greater lateral dimension than said inferior portion to thereby impart a wedge shape to said spacer portion, said spacer having a uniform thickness.

12. An orthopedic implant kit, comprising:
    an orthopedic implant comprising:
    a spacer portion having a superior portion and an inferior portion; and
    a first staple portion, said staple portion being integral with the spacer portion, said first staple portion comprising a first crown portion and first and second leg portions, the first and second leg portions having distal ends that converge from the first crown portion, said first crown portion being connected to the spacer portion proximal said superior portion, the spacer portion extending beyond the first crown portion in the inferior direction generally towards the distal ends of the first and second leg portions;
    at least said first staple portion of said implant comprising a metal material that has superelastic properties at body temperatures, wherein the distal end of the first leg portion is sized to be received within a bone hole in a first bone segment and the distal end of the second leg portion is sized to be received within a bone hole in a second bone segment, wherein said first and second leg portions are configured with inner surfaces that impart a compressive biasing force when the implant is installed with the legs under tension; wherein the spacer portion is configured to maintain a spaced apart relationship between the first and second bone segments, and an insertion tool releasably holding said implant and maintaining said first and second legs in tension.

13. The orthopedic implant kit of claim 12, further comprising a drilling template for positioning pilot shafts in the bone of a patient.

14. The orthopedic implant kit of claim 12, wherein the material of said entire implant is a metal that has superelastic properties at body temperatures.

15. A method for performing a surgical procedure on a patient, comprising:

surgically exposing one or more bones or bone segments;

cutting said at least one or more bones or bone segments to create an opening suitable for insertion of a spacer;

providing the orthopedic implant kit of claim 12;

using said insertion tool to position the spacer in the opening and to position the legs of the staple in at least one of the one or more bones or bone segments of the patient, the legs of the staple imparting a compressive biasing force on said bones or bone segments; and releasing the orthopedic implant from the insertion tool.

* * * * *